United States Patent [19]

Boss et al.

[11] Patent Number: 5,512,583
[45] Date of Patent: Apr. 30, 1996

[54] METHODS OF DECREASING SERUM CALCIUM LEVELS

[75] Inventors: Susan M. Boss, Indianapolis; Willard H. Dere, Carmel, both of Ind.

[73] Assignee: Eli Lilly and Company, Indianapolis, Ind.

[21] Appl. No.: 380,881

[22] Filed: Jan. 30, 1995

[51] Int. Cl.[6] ..................... A61K 31/445; A61K 31/40; A61K 31/38
[52] U.S. Cl. ..................... 514/324; 514/422; 514/443
[58] Field of Search ..................... 514/324, 422, 514/443

[56] References Cited

U.S. PATENT DOCUMENTS

| | | | |
|---|---|---|---|
| 4,133,814 | 1/1979 | Jones et al. | 260/326.55 A |
| 4,380,635 | 4/1983 | Peters | 546/202 |
| 4,418,068 | 11/1983 | Jones | 424/267 |
| 5,075,321 | 12/1991 | Schreiber | 514/317 |
| 5,393,763 | 2/1995 | Black et al. | 514/333 |

FOREIGN PATENT DOCUMENTS

| | | |
|---|---|---|
| 4320896A1 | 6/1993 | Germany . |
| WO93/10113 | 5/1993 | WIPO . |
| WO93/1074 | 6/1993 | WIPO . |

OTHER PUBLICATIONS

U.S. application Ser. No. 07/920,933 filed Jul. 28, 1992 to Black et al.
U.S. application Ser. No. 07/995,222 filed Dec. 22, 1992 to Black et al.
U.S. application Ser. No. 08/035,121 filed Mar. 19, 1993 to Black et al.
U.S. application Ser. No. 08/082218 filed Jun. 24, 1993 to Cullinan et al.
U.S. application Ser. No. 08/096,480 filed Jul. 22, 1993 to Hock.
U.S. application Ser. No. 08/112,012 filed Aug. 15, 1993 to Dodge et al.
U.S. application Ser. No. 08/111,796 filed Aug. 25, 1993 to Dodge et al.
U.S. application Ser. No. 08/081,610 filed Jun. 21, 1993 to Yang.
Draper et al., "Effects of Raloxifene (LY139481 HCl) on Biochemical Markers of Bone and Lipid Metabolism i Healthy Postmenopausal Women", Hong Kong, Fourth Int'l. Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Evans et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti-Estrogen, Simulates the Effects of Estrogen in Inhibiting Bone Resorption Through Regulating TGFB-3 Expression in Bone;" .Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black, L. J. "Biological Actions and Binding Properties of a New Estrogen Antagosist LY117018," In: Homone Antagonists, 129–82, 1982 (M. K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo.

(List continued on next page.)

Primary Examiner—Kimberly Jordan
Attorney, Agent, or Firm—James J. Sales

[57] ABSTRACT

A method of lowering serum calcium levels comprising administering to a human in need thereof an effective amount of a compound having the formula

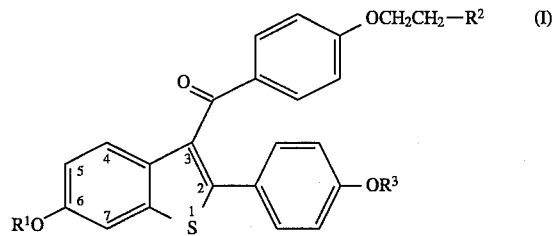

wherein
R[1] and R[3] are independently hydrogen, —CH$_3$,

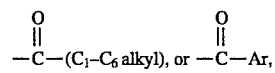

wherein Ar is optionally substituted phenyl;
R[2] is selected from the group consisting of pyrrolidine, hexamethyleneamino, and piperidino; or a pharmaceutically acceptable salt of solvate thereof.

5 Claims, No Drawings

OTHER PUBLICATIONS

Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetcs and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Prince et al., J. Clin. Endorin. and Metab., 72(6) 1226–1228 (1991).

Prince et al., J. Clin. Endorin. and Metab., 71(5) 1284–1287, (1990).

METHODS OF DECREASING SERUM CALCIUM LEVELS

BACKGROUND OF THE INVENTION

Calcium is the most abundant and one of the most important minerals in the human body. Calcium is also an important cation in a wide variety of biological functions such as clotting of blood, the maintenance of normal heart beat and the initiation of neuromuscular and metabolic activities. The skeletal system provides an important reservoir for blood calcium in these processes. More than 99 percent of the calcium in the body is present in the skeleton as hydroxyapatite. Various diseases and metabolic disorders can cause the level of serum calcium to increase or decrease and thus cause serious biochemical and clinical abnormalities.

Of the factors which control calcium and skeletal metabolism, two polypeptide hormones, parathyroid hormone and calcitonin, are considered to be the most important. Parathyroid hormone (PTH) is an 84-amino acid peptide that acts to raise blood calcium and increase bone resorption. Calcitonin is a 32-amino acid polypeptide that acts to decrease bone resorption and lower blood calcium. Calcitonin is produced in the thyroid gland and perhaps at extra thyroidal sites and parathyroid hormone is produced in the parathyroid glands. The half life of calcitonin and of parathyroid hormone in the human body can be measured in minutes.

Hypercalcemia is defined as an excessive quantity of calcium in the blood. Hypercalcemia can occur as a result of numerous different clinical conditions, wherein there are produced high concentrations of free calcium ions in the circulating blood. Causes of hypercalcemia can include, for example, hyperparathyroidism, cancer (with or without bone metastasis), hypervitaminosis D, sarcoidosis, thyrotoxicosis, immobility, and adrenal insufficiency, among others.

Many of the manifestations of hypercalcemia are not specific to the underlying cause. Extreme hypercalcemia leads to coma and death. Neurologic manifestations in less severe cases may include confusion, lethargy, weakness, and hyporeflexia. Hypercalcemia may be detected by shortening of the QT interval on the electrocardiogram. Arrhythmias are rare, but bradycardia and first-degree heart block have been reported. Acute hypercalcemia may be associated with significant hypertension. Gastrointestinal manifestations include constipation and anorexia; in severe cases, there may be nausea and vomiting. Acute pancreatitis has been reported in association with hypercalcemia of various causes. Hypercalcemia interferes with antidiuretic hormone action, thereby leading to polyuria and polydipsia. Reversible reduction in renal function associated with significant hypercalcemia is secretion and action. The active metabolite of vitamin D, 1,25(OH)$_2$D (dihydroxycholecalciferol), suppresses both secretion and synthesis of PTH. Reduction in 1,25(OH)$_2$D is a major factor contributing to increased PTH secretion in renal failure.

Present treatments for hypercalcemia include vigorous intravenous hydration with diuresis to purge calcium from a patient's body. Furthermore, glucocorticoids are also occasionally used in conjunction with such intravenous hydration with diuresis to purge calcium from a patient's body. Other methods which have been utilized to treat hypercalcemia include administering Mithramycin (a chemotherapeutic agent directly toxic to tumor cells and which can decrease plasma calcium levels), administering calcitonin (a hormone from the thyroid which can inhibit bone resorption and thus decrease plasma calcium levels), Etidronate (a chemical compound which binds to calcium phosphate surfaces and inhibits crystal resorption of bone) and administering phosphate. Treatment results with each of the above discussed methods are relatively short lived, and as a consequence, hypercalcemia often readily returns after each of the above discussed treatments are discontinued.

SUMMARY OF THE INVENTION

This invention provides methods for lowering serum calcium levels comprising administering to a human in need thereof an effective amount of a compound of formula I

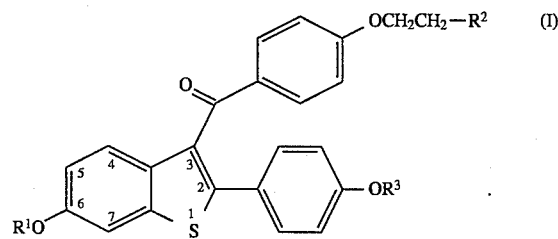

wherein
R$^1$ and R$^3$ are independently hydrogen, —CH$_3$,

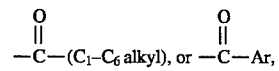

wherein Ar is optionally substituted phenyl;
R$^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for lowering serum calcium level. As such the invention also provides methods for inhibiting hypercalcemia and its effects, and in particular when such is caused by hyperparathyroidism or related to malignancy.

The methods of use provided by this invention are practiced by administering to a human in need thereof a dose of a compound of formula I or a pharmaceutically acceptable salt or solvate thereof, that is effective to lower serum calcium levels.

The term "inhibit" includes its generally accepted meaning which includes prohibiting, preventing, restraining, and slowing, stopping or reversing. As such, the present method includes both medical therapeutic and/or prophylactic administration, as appropriate.

The term "serum calcium level" as used herein, means the level of calcium ions found in the plasma of human patients, and includes calcium which is bonded to proteins and is non-diffusible, as well as calcium which is diffusible and exists in a free ionized form as well as in a complexed form. A suitable method of determining calcium plasma levels is disclosed by Connerty, H. V. and Briggs, A. R., *American Journal of Clinical Pathology*, Vol. 45, p.290 (1986).

Raloxifene, a compound of this invention wherein it is the hydrochloride salt of a compound of formula 1, R$^1$ and R$^3$ are hydrogen and R$^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalane, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The regimen and particular dosage of a compound of formula I required to lower serum calcium levels according to this invention will depend upon the severity of the condition, the route of administration, and related factors that will be decided by the attending physician. Generally, accepted and effective daily doses will be from about 0.1 to about 1000 mg/day, and more typically from about 50 to about 600 mg/day, with a preferred range of 200 to 600 mg/day. Such dosages will be administered to a subject in need thereof from once to about three times each day, or more often as needed, and for a time sufficient to effectively lower the serum calcium level of the patient.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation. 3: Raloxifene capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURE

In Study 1, two hundred fifty one (251) healthy postmenopausal women are assigned to one of four groups:

Group 1—Raioxifene HCl, 200 mg/day;
Group 2—Raloxifene HCl, 600 mg/day;
Group 3—Premarin, 0.625 mg/day; or
Group 4—Placebo.

In Study 2, 167 healthy postmenopausal woman are randomly assigned to one of four groups:

Group 1—Placebo;

Group 2—Raloxifene HCl, 200 mg/day;

Group 3—Raloxifene HCl, 50 mg/day; or

Group 4—Raloxifene HCl, 10 mg/day.

The administration period for the Studies is 8 weeks. For both Studies, clinical laboratory safety assessments include a serum CBC and chemistry panel evaluation at baseline (week 0), and at each return visit (weeks 2, 4, and 8). After completion, the Studies' data are statistically analyzed.

Utility of compounds of the invention is demonstrated by the impact they have on serum calcium levels when used in the Studies above.

We claim:

1. A method of lowering serum calcium levels comprising administering to a human in need thereof an effective amount of a compound having the formula

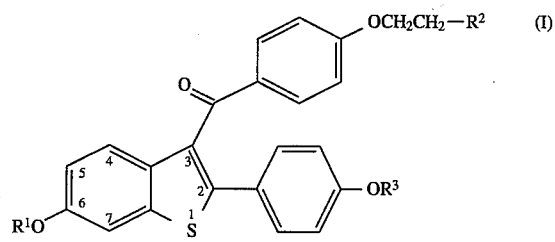

wherein $R^1$ and $R^3$ are independently hydrogen, —$CH_3$,

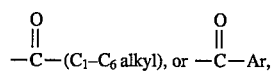

wherein Ar is optionally substituted phenyl;

$R^2$ is selected from the group consisting of pyrrolidine, hexamethyleneminо, and piperidino; or a pharmaceutically acceptable salt of solvate thereof.

2. The method of claim 1 wherein said compound is the hydrochloride salt thereof.

3. The method of claim 1 wherein said compound

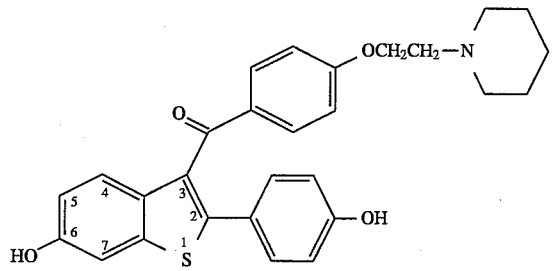

or its hydrochloride salt.

4. The method of claim 1 wherein said human suffers from hypercalcemia.

5. The method of claim 4 wherein said hypercalcemia is caused by hyperparathyroidism or is malignancy-related.

* * * * *